(12) United States Patent
Jackson

(10) Patent No.: US 7,195,643 B2
(45) Date of Patent: Mar. 27, 2007

(54) CONVEX SPINAL FUSION INTERBODY SPACER

(76) Inventor: Roger P. Jackson, 4706 W. 86th St., Prairie Village, KS (US) 66207

( * ) Notice: Subject to any disclaimer, the term of this patent is extended or adjusted under 35 U.S.C. 154(b) by 259 days.

(21) Appl. No.: 10/651,800

(22) Filed: Aug. 29, 2003

(65) Prior Publication Data

US 2005/0049704 A1 Mar. 3, 2005

(51) Int. Cl.
*A61F 2/44* (2006.01)
*A61B 17/56* (2006.01)

(52) U.S. Cl. ..................... 623/17.11; 606/61

(58) Field of Classification Search .. 623/17.11–17.16; 606/61
See application file for complete search history.

(56) References Cited

U.S. PATENT DOCUMENTS

| | | | |
|---|---|---|---|
| 4,834,757 A | 5/1989 | Brantigan | |
| 5,139,527 A | 8/1992 | Redl et al. | |
| 5,192,327 A * | 3/1993 | Brantigan | ............... 623/17.11 |
| 5,425,772 A | 6/1995 | Brantigan | |
| 5,443,514 A | 8/1995 | Steffee | |
| 5,458,638 A | 10/1995 | Kuslich et al. | |
| 5,489,308 A | 2/1996 | Kuslich et al. | |
| 5,554,191 A | 9/1996 | Lahille et al. | |
| 5,609,636 A | 3/1997 | Kohrs et al. | |
| 5,658,337 A | 8/1997 | Kohrs et al. | |
| 5,665,122 A | 9/1997 | Kambin | |
| 5,669,909 A | 9/1997 | Zdeblick et al. | |
| 5,681,135 A | 10/1997 | Simonson | |
| 5,693,100 A | 12/1997 | Pisharodi | |
| 5,716,355 A | 2/1998 | Jackson et al. | |
| 5,716,415 A | 2/1998 | Steffee | |
| 5,782,919 A | 7/1998 | Zdeblick et al. | |
| 5,865,847 A | 2/1999 | Kohrs et al. | |
| 5,904,719 A | 5/1999 | Errico et al. | |
| 5,941,880 A | 8/1999 | Errico et al. | |
| 5,968,098 A | 10/1999 | Winslow | |
| 5,980,552 A | 11/1999 | Koros et al. | |
| 6,059,829 A * | 5/2000 | Schlapfer et al. | ......... 623/17.16 |
| 6,102,950 A | 8/2000 | Vaccaro | |
| 6,117,174 A | 9/2000 | Nolan | |
| 6,123,705 A | 9/2000 | Michelson | |
| 6,129,763 A | 10/2000 | Chauvin et al. | |
| 6,165,219 A | 12/2000 | Kohrs et al. | |
| 6,176,882 B1 | 1/2001 | Biedermann et al. | |
| 6,206,922 B1 | 3/2001 | Zdeblick et al. | |
| 6,224,631 B1 * | 5/2001 | Kohrs | ................ 623/17.11 |
| 6,290,724 B1 * | 9/2001 | Marino | ................ 623/17.11 |
| 6,325,827 B1 | 12/2001 | Lin | |
| 6,436,139 B1 | 8/2002 | Shapiro et al. | |
| 6,440,170 B1 * | 8/2002 | Jackson | ................ 623/17.16 |

\* cited by examiner

*Primary Examiner*—David J. Isabella
(74) *Attorney, Agent, or Firm*—John C. McMahon

(57) ABSTRACT

A convex spinal fusion interbody space device includes spaced apart superior and inferior abutment surfaces which are effectively medially convex. The peak of such convexity is displaced anteriorly of a central plane through the device. The spacer device has a height which is greater than the width of the device. The spacer device is implanted between a pair of adjacent vertebrae by insertion in a tipped-over orientation and then reoriented to an upright orientation for engagement by facing surfaces of the vertebrae. Fusion promoting bone material is packed between the vertebrae and about and within the spacer device subsequent to implantation.

26 Claims, 3 Drawing Sheets

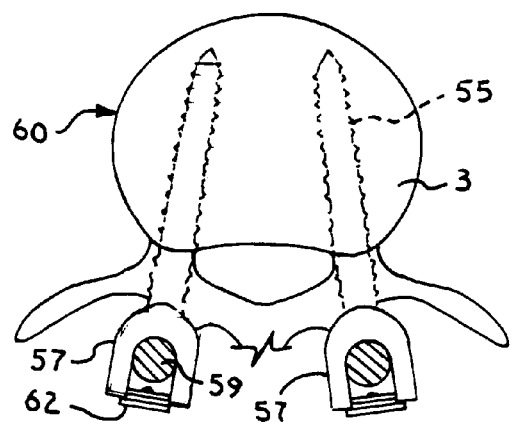
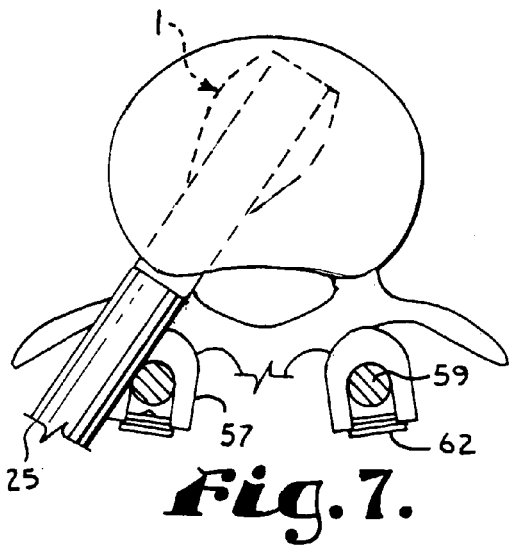
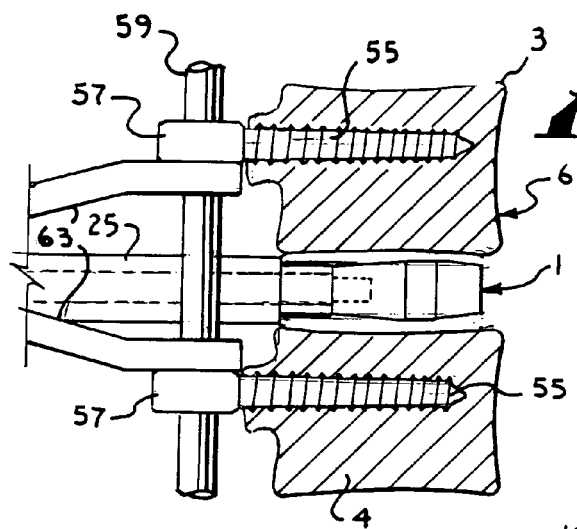
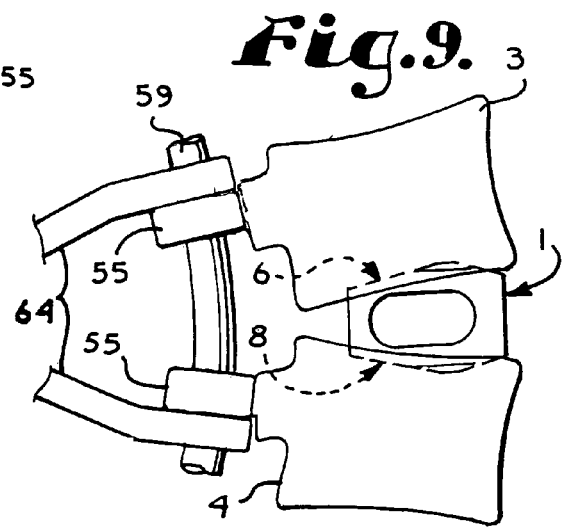

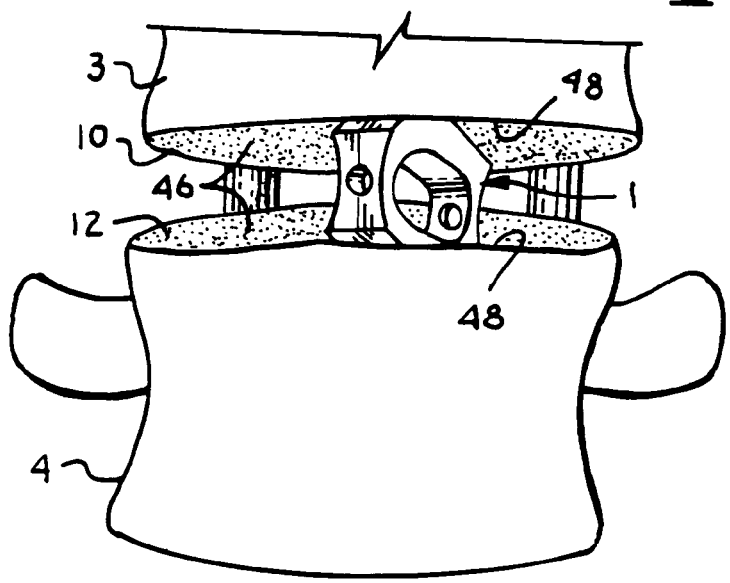
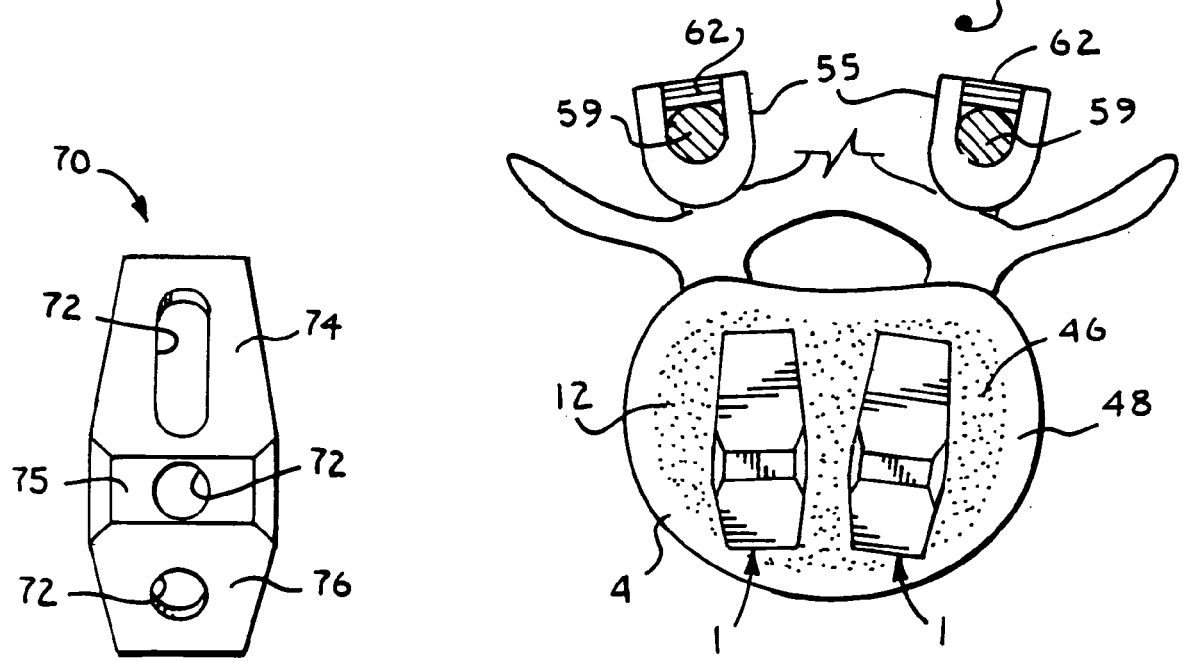

CONVEX SPINAL FUSION INTERBODY SPACER

BACKGROUND OF THE INVENTION

The present application is directed to an interbody device for implantation between a pair of adjacent vertebrae in order to provide support to the vertebrae and/or promote bone fusion between the vertebrae and, in particular, to a non threaded and non cylindrical interbody device having opposed concave sides and a front to rear convex or trapezoidal configuration.

In the human spine the pad or disc between vertebrae is sometimes damaged or deteriorates due to age, disease, injury, or congenital defect. The vertebrae may also become compressed or otherwise damaged. Vertebrae often become too closely anteriorly spaced due especially to age but also other factors that generally produces an abnormal curvature with respect to lordosis or kyphosis, which is undesirable. Because of this, surgery is often utilized to place spacers or interbody devices between the vertebrae which provide proper spacing of the vertebrae and which also promote fusion between the vertebrae. When a device of this type is utilized for purposes of promoting fusion, it is often referred to as a fusion cage or an intervertebral fusion device. When utilized to promote fusion, the interbody devices sometimes are windowed or fenestrated and packed with bone fusion material to promote growth of the bone between the vertebrae. Sometimes such material is packed between a pair of devices that are placed in close proximity to one another between the vertebrae to promote growth of bone and, therefore, fusion between the vertebrae.

In the past, interbody devices have typically been either generally rectangular or cylindrical and threaded in shape. The cylindrical devices have an advantage in that they can be threadably received more or less directly between and into the adjacent vertebrae. For this purpose, the vertebrae are typically first spaced apart, and then a drill is utilized to create a partial bore (radiused channel) in each vertebra which allows this type of interbody device to be received between the vertebrae. Because of the space between the bones, the interbody device usually engages the bones only along an upper surface and a lower surface thereof. When the interbody device is of a cylindrical threaded type, the upper and lower surfaces are radiused relative to a front to rear axis and such are essentially designed to engage the portion of the vertebrae where bone is unremoved by boring to create an opening for the device.

When interbody devices are used, it is desirable that the device engages as much surface of bone as possible to provide support to the bone and to reduce the likelihood of subsidence of the device into the bone, resulting from contact pressure of the interbody spacer relative to an intervertebral surface of a vertebra, since part of the bone is somewhat spongy in nature, especially near the center of the upper and lower surfaces of the bones. The remainder of the structure mainly functions to support the two surfaces, unless the device is also used as a cage within which to pack bone fusion material. Because it is also desirable in such structures to maintain weight and volume as low as possible, in order to make the device more compatible with the body, it is also desirable to make the entire device as small and lightweight as possible, while maintaining strength.

It is also desirable to minimize the amount of cutting into and reshaping of the vertebral bones to only that which is necessary to correct the structure and function of the spine. Thus, it would be desirable to conform an interbody spacer to the shape of the intervertebral surfaces of adjacent vertebrae, which is shallowly concave, if possible in a given circumstance, rather than conform the vertebrae to the shape of the interbody spacer.

Finally, as noted above, age and injury cause the vertebrae to somewhat anteriorly collapse over time. Therefore, it is also desirable for such an interbody spacer to correctly space the vertebrae anteriorly so as to promote normal lordosis or curvature with respect to the spine.

SUMMARY OF THE INVENTION

The present invention provides an interbody or intervertebral spacer device for placement between a pair of spaced, but adjacent, vertebrae that is generally convex or sloped between the anterior and posterior ends (that is between front and rear or along the longitudinal axis), preferably on both the top and bottom, so as to generally conform with the slope or desired shape and positioning of the surfaces of the vertebrae that are engaged by the device. The spacer has mirror image convex inferior and superior bearing or abutment surfaces adapted to engage the somewhat concave end plate surfaces of adjacent vertebrae. Preferably, the top and bottom convexity of the spacer between front and rear or along the central axis thereof substantially matches the concavity of the end plate surfaces whereat the spacer is to be located during usage, such that maximum surface contact occurs and so that maximum support is provided to reduce the likelihood of subsidence, while encouraging normal lordosis of the spine. In particular, the convexity of the abutment surfaces peaks at a location which is somewhat anterior of a medial plane between anterior and posterior end surfaces of the interbody spacer.

Although in some embodiments the abutment surfaces may be rounded and continuous or arced from front to rear, the interbody spacer in some embodiments has faceted abutment surfaces, each formed by a peak surface, an anterior inclined surface, and a posterior inclined surface so as to form an overall arced engagement or abutment surface. The abutment surface may also include lateral bevels formed at lateral ends of the peak surface. The anterior and posterior end surfaces are planar and generally parallel. Lateral surfaces of the interbody spacer are preferably cylindrical and concave to reduce volume and weight. Preferably, a central cavity is formed through the interbody spacer from one lateral surface to the other, although the cavity may be eliminated where there is sufficient room about the spacer to pack bone growth material or where additional strength is required. The central cavity is intended to receive bone growth or fusion promoting material between the bone of the adjacent vertebrae between which the spacer is positioned. Alternatively, other openings and apertures can be formed in the spacer, such as through the facets of the abutment surfaces to receive bone growth. In some embodiments the end surfaces are provided with threaded bores to receive an installation tool employed to implant the interbody spacer between an adjacent pair of vertebrae.

The ends of the inferior and superior abutment surfaces are spaced apart by a nominal height dimension, while the lateral surfaces are separated at their closest by a nominal width or thickness dimension. The interbody spacer of the present invention has a height dimension which is greater than the width dimension. Because the mutually facing surfaces of the end plates of an adjacent pair of vertebrae are concave, the peripheral edges are closer than central portions of the end plate surfaces.

The present invention includes a method of implanting interbody spacers comprising spreading the adjacent pair of vertebrae a distance somewhat greater than the width of the interbody spacer, insertion of the spacer into the intervertebral space in an orientation with the lateral surfaces of the spacer facing the end plates of the adjacent vertebrae and thereafter rotation of the spacer about a longitudinal axis to orient the abutment surfaces into facing relation relative to the end plates of the vertebrae. The vertebrae are then allowed to seat on the abutment surfaces. The position of the spacer may then be adjusted as necessary and spinal fusion promoting bone material positioned between the vertebrae and within the central opening. In some methods of use, only a single spacer is used with other posterior implant support structure. In other circumstances, it is desirable to implant a pair of laterally spaced interbody spacers between the vertebrae for stability and strength.

Preferably, the spacer is used in conjunction with other implants including bone screws mounted in the vertebrae and tightly attached at the end of the procedure to a rod or rods that extend along the spine. The bone screws and, consequently, the associated vertebrae are positioned at the end of the insertion procedure so as to urge the vertebrae into engagement with the spacer and thereby secure the position of the spacer and help or cooperate with the spacer to favorably adjust the lordosis of the vertebrae, while securely locating the adjacent vertebrae relative to one another so as to promote fusion.

Interbody devices of the type used herein must be compatible with implantation in the human body. Such devices include biologically active implants such as made of boney material, coral or other biologically active material where the vertebral bone grows through the material of the implant and over time replaces part or all of the implant by creeping substitution and biologically inactive materials such as metals, plastics and the like.

OBJECTS AND ADVANTAGES OF THE INVENTION

Therefore, the objects of the present invention include: providing an interbody spacer or fusion cage device having convex upper and lower bearing or abutment surfaces for implanting between a pair of adjacent vertebrae to properly space the vertebrae and/or to promote fusion between the vertebrae; providing such a device in which the peak of convexity of the abutment surfaces is positioned somewhat anterior of a medial plane midway between anterior and posterior surfaces of the spacer; providing such a device in which the convex abutment surfaces are formed by planar facets, including a peak facet, an anterior inclined facet, and a posterior inclined facet, all as a single unit or unitary piece; providing such a device formed of a material which is appropriate to the long term disposition of the device desired, such as a biologically inactive metallic material, a biologically inactive non-metallic material, a biologically active bone-based material, or a biologically active non-bone-based material; providing such a device having cylindrically concave lateral or side surfaces that join the upper and lower abutment surfaces on opposite lateral sides of the device; providing such a device wherein the structure of the interbody spacer device is strong, while minimizing volume and weight; providing such a device that can be either solid or partly hollow in order to allow packing with bone chips or other bone fusion promoting materials; providing such a device which enables relatively close spacing of a pair of devices in side by side relationship; providing such a device that enables a substantial opening between a pair of devices in side by side relationship to facilitate packing with bone chips and subsequent fusion between the vertebrae associated with the devices; providing such an interbody spacer device which minimizes surgical alteration of the vertebral bones between which the spacer is implanted; providing a method of implanting such a device between a pair of adjacent vertebrae including spreading the adjacent vertebrae apart a distance somewhat greater than the lateral width of the spacer, insertion of the spacer between the vertebrae in a laterally tipped over orientation, and rotating so as to reorient the spacer to an upright position to engage the upper and lower abutment surfaces with facing end plate surfaces of the adjacent vertebrae and thereafter using other implants to compress the posteriors of the vertebrae toward one another to clamp the device in place; and to provide such a device which is economical to manufacture, which is relatively simple to implant, which is efficient in operation, and which is particularly well suited for its intended usage.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 6 is a view similar to FIG. 5 and illustrates details of spinal fixation structure which supports the implantation of the interbody spacer device of the present invention.

FIG. 7 is a view similar to FIG. 6 and illustrates a spacer installation tool used to implant the interbody spacer device in a laterally tipped over orientation between an adjacent pair of the vertebrae.

FIG. 8 is a fragmentary side elevational view illustrating the spacer installation tool with an interbody spacer device still joined thereto.

FIG. 9 is a view similar to FIG. 8 and illustrates the interbody spacer device rotated ninety degrees to an upright orientation and spinal fixation rods compressed to position the adjacent vertebrae in a desired relationship.

FIG. 10 is a view similar to FIG. 4 and illustrates the interbody spacer device implanted between an adjacent pair of vertebrae and the posterior spacing between the vertebrae comparatively reduced by manipulation of bone screws along rods.

FIG. 11 is a view similar to FIG. 5 and illustrates a an alternative use embodiment with a pair of the interbody spacer devices positioned in side by side relation between a pair of vertebrae.

FIG. 12 is a somewhat enlarged top plan view of a modified embodiment of the interbody spacer device with openings formed in facets of the upper and lower abutment surfaces to receive bone fusion promoting material.

DETAILED DESCRIPTION OF THE INVENTION

Figure 1:
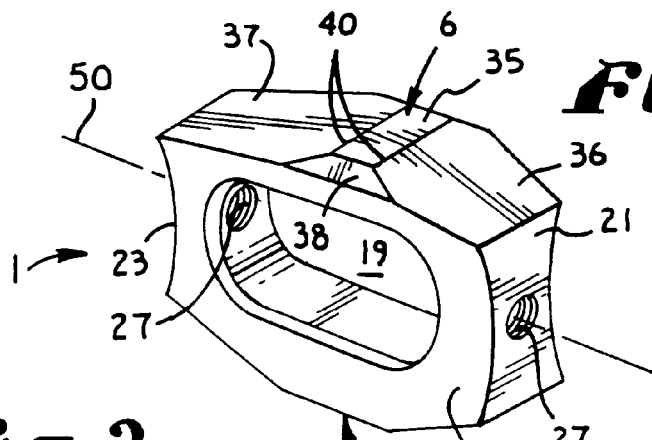
FIG. 1 is an enlarged perspective view of a convex spinal fusion interbody spacer device embodying the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally designates a convex spinal fusion interbody spacer device which embodies the present invention. The device 1 is used to maintain proper spacing between a pair of adjacent vertebrae 3 and 4 of a human spine as a replacement for the intervertebral disc and to promote fusion between the vertebrae 3 and 4, preferably in conjunction with other implants, as noted below. In particular, the device 1 has a superior (or upper) surface 6 and an inferior (or lower) surface 8 which surfaces 6 and 8 are arced or convex or effectively convex when viewed from the side, such as in FIG. 2. The convexity of the abutment or bearing surfaces 6 and 8 is fixed or rigid and conforms to the natural concavity of the mutually facing surfaces 10 and 12 of end plates of the adjacent vertebrae 3 and 4. The device 1 is constructed from a single, unitary and rigid blank and has a fixed shape that is medially bowed outwardly at the top and bottom, preferably forward of a front to rear center of the device 1, as discussed below. In some embodiments the device 1 is tear shaped, fish shaped or fusiform in nature.

The illustrated spacer device 1 includes top and bottom walls or sections 14 and 15 and front and back walls or sections 16 and 17, forming an outer elongate ring 18 surrounding an inner opening or cavity 19. The superior abutment surface 6 is formed on the outer side of the top wall 14, while the inferior abutment surface 8 is formed on the outer side of the lower wall 15. The front wall 16 and back wall 17 have respective anterior and posterior outer end surfaces 21 and 23. The end surfaces 21 and 23 are illustrated as planar, although it is foreseen that they could be an alternative shape. The illustrated spacer device 1 includes tool engagement formations to enable positive engagement by an installation tool 25 (FIGS. 7 and 8), such as threaded bores 27 formed through the end walls 16 and 17.

Figure 2:
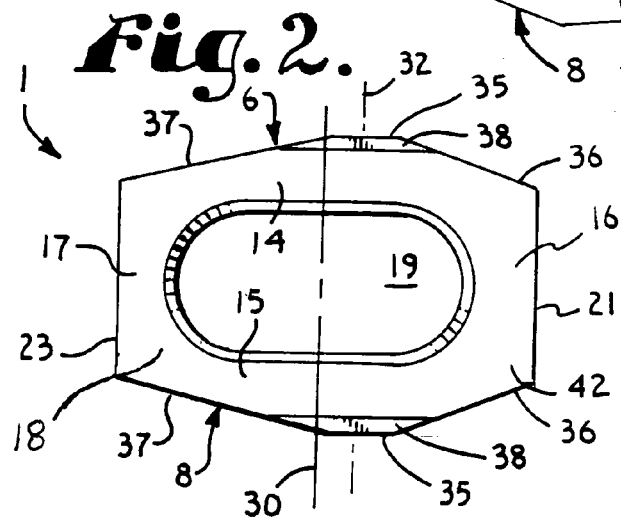
FIG. 2 is a side elevational view of the spacer device illustrating an anteriorly displaced convex peak of the device.

The preferred spacer device 1 of the present invention is not symmetrical, when viewed from either side. FIG. 2 illustrates a front to rear middle plane 30 positioned halfway between the end surfaces 21 and 23 and parallel thereto, which bisects the device 1 from front to back with the front or anterior end thereof being to the right in FIG. 2. Also illustrated is a "convexity" plane 32 positioned at a medial location of the peak convexity of the abutment surfaces 6 and 8, thus, representing the location of such peak convexity. The imaginary convexity plane 32 is located in spaced relationship to the end surfaces 21 and 23 such that the vertical height of the device 1 at the location of the plane 32 is greater than the height of either end surface 21 or 23. In the illustrated embodiment the height of the end surfaces 21 and 23 is essentially the same, although it is foreseen that one may have a greater height than the other, especially the front end surface 21 may have a height greater than the rear end surface 23.

In particular, as illustrated, the convexity plane 32 is positioned closer to the anterior end surface 21 (about 40% of total length from anterior end to plane 32) than to the posterior end surface 23 and is, thus, spaced anteriorly of the middle plane 30. The reason for the anteriorly shifted or displaced asymmetry of the convexity of the device 1 is to more closely conform the shape of the abutment surfaces 6 and 8 to the concavity of the vertebral end plate surfaces 10 and 12, preferably in a correct lordotic alignment of the vertebrae 3 and 4. Such shape conformance respectively between the abutment surfaces 6 and 8 and the vertebral surfaces 10 and 12 tends to maximize bearing engagement therebetween and tends to minimize possible subsidence of the device 1 into the vertebrae 3 and 4, while providing greater spacing between the anterior ends of the vertebrae 3 and 4 than the posterior ends thereof (see FIG. 9).

The illustrated abutment surfaces 6 and 8 are formed by multiple component surfaces or facets, including a peak facet 35, an anterior or front facet 36, and a posterior or rear facet 37. However, it is foreseen in certain circumstances that the surfaces 6 and 8 may be formed by a continuous or even discontinuous curved surface or by other suitable elements forming a surface that will generally conform to the concavity of the lower and upper surface of the vertebrae 3 and 4 respectfully. The surfaces 6 and 8 may also include lateral facets or bevels 38. In certain embodiments it is foreseen that the sides of the surfaces may be curved or radiused to meet the sides of the device 1 to promote rotation during installation. Because the plane of convexity 32 is displaced anteriorly of the middle plane 30, the anterior facet 36 is shorter than the posterior facet 37.

As noted above the illustrated abutment surfaces 6 and 8 are faceted, but such could alternatively be formed by continuous, curved surfaces. With the faceted surfaces the edges 40 formed by intersection of the facets 35–37 provide a small measure of gripping engagement with the vertebral surfaces 10 and 12 to hold the devices 1 in place and in the desired orientation between the adjacent vertebrae 3 and 4 until fusion between the vertebrae 3 and 4 occurs. Additionally, the abutment surfaces 6 and 8 are somewhat more easily and more accurately formed by the facets 35–38 in a machining process than would be possible with a compound curved contour of the surfaces 6 and 8.

Figure 3:
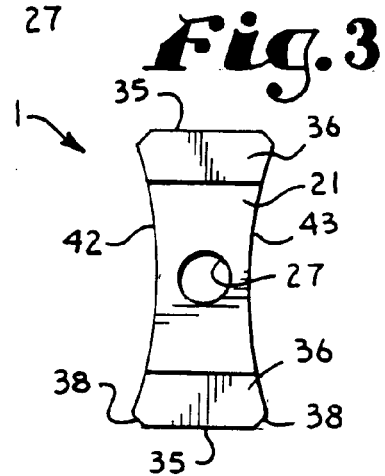
FIG. 3 is an end elevational view of the interbody spacer device.
Figure 4:
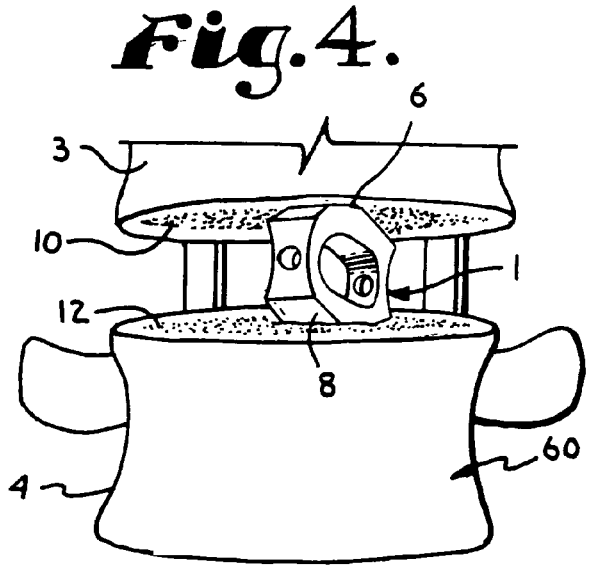
FIG. 4 is a fragmentary elevational view at a reduced scale of the device and illustrates the device implanted between an adjacent pair of vertebrae.
Figure 5:
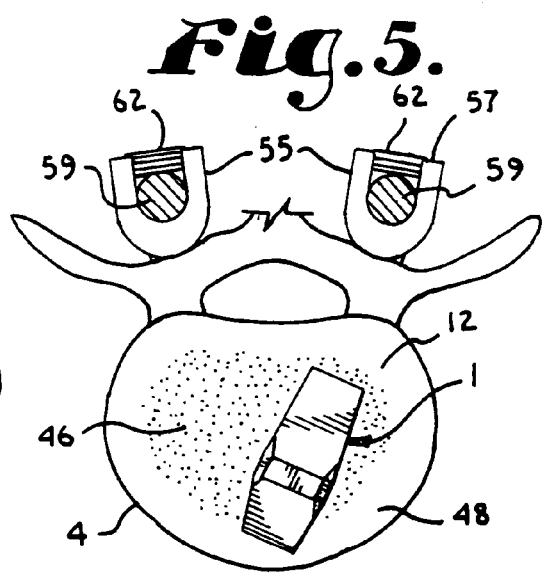
FIG. 5 is a top plan view of the interbody spacer device implanted between the pair of vertebrae.

Referring to FIGS. 1 and 3, the interbody spacer device 1 has side or lateral surfaces 42 and 43. Although it is foreseen that the side surfaces could be planar or other shapes, the illustrated side surfaces 42 and 43 are inwardly cylindrical or concave towards the longitudinal or front to rear axis. The concavity of the surfaces 42 and 43 results in a weight reduction in the device 1 without appreciably reducing its strength, apparently due to the arches and lack of stress risers formed thereby. Additionally, the concave shape leaves more volume between the adjacent vertebrae 3 and 4 to receive fusion promoting bone material. The opening 19 is formed through the device 1 from side surface 42 to side surface 43 and it is foreseen that such an opening 19 may not be included in all embodiments or that other types of single or multiple openings may be utilized. The illustrated opening 19 is oval in shape, although it is foreseen that other shapes could also be employed. The opening 19 provides an open volume for receiving the fusion promoting material and does not materially reduce the strength of the device 1.

The device 1 can be formed from any material which has suitable structural properties, which is biologically non harmful, and which does not promote the growth of pathogens. The material of construction can be biologically active or inactive as discussed in greater detail below. For example, various types of stainless steel are suitable as materials of construction. In the illustrated embodiment, the device 1 is formed of a carbon fiber reinforced composite. Such composites are available which satisfy the structural and biological requirements. The device 1 can be formed by molding, by machining, cutting, or the like, or by a combination of such processes to preferably form a single or unitary structure, preferably with no parts that are moveable relative to other parts thereof.

The present invention includes novel methods of implanting a spinal fusion spacer device 1 between a pair of adjacent vertebrae 3 and 4. Referring to FIG. 3, the device 1 has a height dimension measured between the upper and lower peak facets 35 and a width or thickness dimension represented by the facets 36 or 37 at their widest. As can be observed from the frontal view shown in FIG. 3, the height dimension of the device 1 exceeds its width by a considerable extent. In the illustrated embodiment the height at plane 32 is about 2.2 times the maximum side to side width. It should be noted that the upright orientation of the device 1 shown in FIGS. 1–5 and 9–11 is the operational orientation of the spacer device 1 in which the device 1 performs the function thereof as a spacer between the vertebrae 3 and 4.

As stated previously, the facing surfaces 10 and 12 of the vertebrae 3 and 4 are somewhat concave in that most of the interior or central regions 46 (FIG. 10) of the surfaces 10 and 12 are spaced farther apart than edge regions 48 of the surfaces 10 and 12. In order to implant a device 1 between the vertebrae 3 and 4, it is preferable to position the vertebrae 3 and 4 far enough apart so that the device 1 can be inserted therebetween at least sideways and then rotated. Insertion is most often by a posterior approach, but may be from any direction selected by the surgeon. In the present invention, the vertebrae 3 and 4 are spread apart during the surgical procedure a sufficient distance that the device 1 can be inserted between the edge regions 48 in a laterally laid-over or tipped-over orientation (see FIGS. 7 and 8) and then rotated to the upright orientation shown particularly in FIGS. 1, 4, and 10. The device 1 is inserted between the vertebrae 3 and 4 in a tipped-over orientation to the eventual use location thereof and then rotated only ninety degrees (as opposed to screwing completely into place as is the case of many cylindrical cages) about a longitudinal axis 50 (FIG. 1) passing through the threaded bores 27.

Most specifically, with respect to the procedure and referring to FIGS. 5–9, a pair of open-headed bone screws 55 are threadedly implanted into each of the vertebrae 3 and 4. Open heads 57 of the screws 55 are aligned to receive spinal fixation rods 59 which run lengthwise along at least a portion of the spine 60 of which the vertebrae 3 and 4 are components. The bone screw heads 57 receive closure plugs 62 which, when tightened, secure the rods 59 within the heads 57. The heads 57 and plugs 62 may employ cooperating helical guide and advancement mechanisms to advance the plugs 62 into engagement with the rods 59, as the plugs 62 are rotated into the heads 57. Details of open-headed bone screws 55 and closure plugs 62 which would be appropriate for use with the device 1 can found in U. S. Pat. No. 6,004,349, which is incorporated herein by reference. Initially the rods 59 are captured only loosely in the heads 57 by the plugs 62, so as to allow movement of the screws 55 along the rods 59 under control of the surgeon.

The vertebrae 3 and 4 are spaced a desired distance by use of a scissors like spreader tool 63 (partially seen in FIG. 8), and the plugs 62 may be lightly tightened into engagement with the rods 59. The desired intervertebral distance is such a distance which enables insertion of the spacer device 1 therebetween in the tipped-over orientation (FIG. 8) and then uprighting of the device 1 (FIG. 10) by ninety degree rotation and reorientation to the upright orientation. The spacer device 1 is inserted between the spread vertebrae 3 and 4 in the tipped-over orientation and rotated to the upright orientation using the installation tool 25; then the tool 25 is detached from the device 1.

The plugs 62 are then loosened and a compression tool 64 (see FIG. 9) is used to urge the screws 55 of adjacent vertebrae 3 and 4 toward each other so that the posterior ends of the vertebrae 3 and 4 become more closely spaced to allow the inner surfaces 10 and 12 respectively thereof to engage the upper and lower abutment surfaces 6 and 8 of the device 1, preferably in a snug or clamping relationship. This clamping secures the device 1 in the position selected therefor between the vertebrae 3 and 4. The orientation of the device 1 about an axis parallel to the spine 60 is adjusted, if necessary prior to final tightening of the plugs 62 to lock the relative position between the rod 59 and screws 55. The rods 59 may be bent somewhat to achieve a desired angular or lordotic relationship between the vertebrae 3 and 4, as shown in FIG. 9. A single device 1 when used in conjunction with a pair of bone screws 55 in each vertebrae 3 and 4 forms a solid multiple point of support so as to stabilize the vertebrae 3 and 4 with respect to each other. In the illustrated embodiment there is a stable three point support provided for each vertebrae 3 and 4 relative to its adjacent vertebrae 3 or 4.

In an alternative usage, the implantation procedure may also include the insertion of a second spacer device 1 between the vertebrae 3 and 4 in laterally spaced relation thereto.

When the desired degree of engagement between the vertebrae 3 and 4 and one or two of the devices 1, along with the desired orientation of the devices 1 and the vertebrae 3 and 4 is achieved, the closure plugs 62 are advanced into secure engagement with the rods 59 in a substantially permanent relation. Such an embodiment provides four points of support for each vertebrae 3 and 4 relative to the adjacent vertebrae 3 or 4.

Any voids between the vertebrae 3 and 4 and within the device or devices 1 are preferably packed with bone material which, over time, will promote fusion between the vertebrae 3 and 4 in the spacing and orientations established by the spacer device 1 and the fixation rods 59.

FIG. 12 illustrates a modified embodiment 70 of the spacer device of the present invention. The modified device 70 is provided with openings 72 formed through facets 74, 75, and 76. The openings 72 are provided to receive fusion promoting bone material after implanting the device 70 between a pair of adjacent vertebrae 3 and 4. In other respects, the modified device 70 is substantially similar to the spacer device 1.

The devices 1 and 70 preferably include no moving or adjustable parts, are non-threaded, and include no fins to cut into the bone. The devices 1 and 70 may be manufactured from biologically inactive materials or from biologically active materials which are compatible with implantation. The devices 1 and 70 formed of biologically inactive materials are chemically and biologically essentially inert in their implanted environments. Fusion of the vertebrae 3 and 4 occurs around the device 1 and 70 and through respective structural openings formed through the devices 1 and 70; however, the devices 1 and 70 remain intact after implantation. The biologically inactive materials used for the devices 1 and 70 can be divided into metallic materials and non-metallic materials.

Metallic biologically inactive materials may include certain alloys of stainless steel, titanium, and tantalum and other alloys which are structurally, chemically, and biologically appropriate. Non-metallic biologically inactive materials for the devices 1 and 70 can include certain plastics or polymers, organic and inorganic resins, composites, and ceramics, especially polyester ketone or the polymer commonly referred to as "pek". The polymers are preferably non-porous, with bone fusion occurring through the openings 10 or 72 of the devices 1 and 70. The composites may include carbon fiber reinforced materials. Appropriate ceramics are preferably porous and can be of an "open scaffold" type which allow bone fusion growth through the ceramic material itself.

The devices 1 and 70 can also be formed from biologically active materials which are normally substituted for, absorbed, or otherwise replaced as bone fusion of the vertebrae 3 and 4 proceeds. The biologically active materials can be either bone-based or non-bone-based. The term bone-based material is used herein to refer to a material which is made from actual bones, bone derivatives, or materials which are chemically bone-like. Bones are typically formed mostly (about 85 percent) of tri-basic calcium phosphate which, in living bone, is called hydroxy-apatite or simply calcium phosphate. In general, the bone is formed by cutting, machining or the like or bone derived material is ground, mixed with a suitable resin or other binder, and cast, molded or machined to shape. Further machining or other mechanical forming may be performed in final shaping of formed implant spacers. The source of bone for such material is possibly from the patient who will receive the implant or from cadaver bone or allograft. Other sources may include non-human bone.

Biologically active, non-bone-based materials appropriate for use in the devices 1 and 70 include corals, certain resins and similar materials. The principal constituent of coral is calcium carbonate in a porous form which allows bone fusion growth through the resulting spacer. The devices 1 and 70 can be formed of coral by machining or carving processes. The coral material is normally replaced over time by biological processes in the body, as the spinal fusion process occurs.

Although the illustrated embodiment shows the devices 1 and 70 being inserted fully from the posterior and then rotated ninety degrees, it is foreseen that the devices 1 and 70 could be inserted anteriorly or from the side.

It is also foreseen that in certain embodiments, the greatest height of the device may be at an anterior end thereof, as required in some situations to produce correct spinal curvature, such that the device has a generally trapezoidal side profile.

It is to be understood that while certain forms of the present invention have been illustrated and described herein, it is not to be limited to the specific forms or arrangement of parts described and shown.

What is claimed and desired to be secured by Letters Patent is as follows:

1. A biologically inactive non-metal spinal fusion interbody spacer comprising:
   (a) an anterior end surface and an opposite posterior end surface spaced from said anterior end surface;
   (b) a superior abutment surface and an opposite inferior abutment surface spaced from said superior abutment surface, said superior and inferior abutment surfaces extending respectively between said anterior and posterior end surfaces;
   (c) a center reference plane positioned substantially equidistant between said anterior and posterior end surfaces and intersecting said superior and inferior abutment surfaces;
   (d) each of said abutment surfaces being effectively convex and having a respective peak of convexity located at a position spaced substantially anterior of said center reference plane;
   (e) at least one of said abutment surfaces is formed by a plurality of substantially planar facets; and
   (f) said spacer being formed from a non-metallic material which is biologically inactive.

2. A biologically inactive non-metal spinal fusion interbody spacer comprising:
   (a) an anterior end surface and an opposite posterior end surface spaced from said anterior end surface;
   (b) a superior abutment surface and an opposite inferior abutment surface spaced from said superior abutment surface, said superior and inferior abutment surfaces extending respectively between said anterior and posterior end surfaces;
   (c) a center reference plane positioned substantially equidistant between said anterior and posterior end surfaces and intersecting said superior and inferior abutment surfaces;
   (d) each of said abutment surfaces being effectively convex and having a respective peak of convexity located at a position spaced substantially anterior of said center reference plane;
   (e) each of said abutment surfaces is formed by a plurality of substantially planar facets; and
   (f) said spacer being formed from a non-metallic material which is biologically inactive.

3. A biologically inactive non-metal spinal fusion interbody spacer comprising:
   (a) an anterior end surface and an opposite posterior end surface spaced from said anterior end surface;
   (b) a superior abutment surface and an opposite inferior abutment surface spaced from said superior abutment surface, said superior and inferior abutment surfaces extending respectively between said anterior and posterior end surfaces;
   (c) a center reference plane positioned substantially equidistant between said anterior and posterior end surfaces and intersecting said superior and inferior abutment surfaces;
   (d) each of said abutment surfaces being effectively convex and having a respective peak of convexity located at a position spaced substantially anterior of said center reference plane;
   (e) a pair of laterally opposite side surfaces;
   (f) each of said opposite side surfaces is substantially concave; and
   (g) said spacer being formed from a non-metallic material which is biologically inactive.

4. A biologically inactive non-metal spinal fusion interbody spacer comprising:
   (a) an anterior end surface and an opposite posterior end surface spaced from said anterior end surface;
   (b) a superior abutment surface and an opposite inferior abutment surface spaced from said superior abutment surface, said superior and inferior abutment surfaces extending respectively between said anterior and posterior end surfaces;

(c) a center reference plane positioned substantially equidistant between said anterior and posterior end surfaces and intersecting said superior and inferior abutment surfaces;

(d) each of said abutment surfaces being effectively convex and having a respective peak of convexity located at a position spaced substantially anterior of said center reference plane;

(e) a pair of laterally opposite side surfaces;

(f) each of said opposite side surfaces being substantially concave and cylindrical; and (g) said spacer being formed from a non-metallic material which is biologically inactive.

5. A biologically inactive non-metal spinal fusion interbody spacer comprising:

(a) an anterior end surface and an opposite posterior end surface spaced from said anterior end surface;

(b) a superior abutment surface and an opposite inferior abutment surface spaced from said superior abutment surface, said superior and inferior abutment surfaces extending respectively between said anterior and posterior end surfaces;

(c) a center reference plane positioned substantially equidistant between said anterior and posterior end surfaces and intersecting said superior and inferior abutment surfaces;

(d) each of said abutment surfaces being effectively convex and having a respective peak of convexity located at a position spaced substantially anterior of said center reference plane;

(e) at least one opening for receiving a bone fusion material to promote fusion between a pair of adjacent vertebrae; and (f) said spacer being formed from a non-metallic material which is biologically inactive.

6. A biologically inactive non-metal spinal fusion interbody spacer comprising:

(a) an anterior end surface and an opposite posterior end surface spaced from said anterior end surface;

(b) a superior abutment surface and an opposite inferior abutment surface spaced from said superior abutment surface, said superior and inferior abutment surfaces extending respectively between said anterior and posterior end surfaces;

(c) a center reference plane positioned substantially equidistant between said anterior and posterior end surfaces and intersecting said superior and inferior abutment surfaces;

(d) each of said abutment surfaces being effectively convex and having a respective peak of convexity located at a position spaced substantially anterior of said center reference plane;

(e) a pair of laterally opposite side surfaces spaced apart by an effective width dimension;

(f) said superior and inferior abutment surfaces being spaced apart an effective height dimension;

(g) said height dimension being greater than said width dimension; and (e) said spacer being formed from a non-metallic material which is biologically inactive.

7. A biologically inactive non-metal spinal fusion interbody spacer comprising:

(a) an anterior end surface and an opposite posterior end surface spaced from said anterior end surface;

(b) a superior abutment surface and an opposite inferior abutment surface spaced from said superior abutment surface, said superior and inferior abutment surfaces extending respectively between said anterior and posterior end surfaces;

(c) a center reference plane positioned substantially equidistant between said anterior and posterior end surfaces and intersecting said superior and inferior abutment surfaces;

(d) each of said abutment surfaces being effectively convex and having a respective peak of convexity located at a position spaced substantially anterior of said center reference plane;

(e) a tool engaging formation to enable positive engagement of a tool with said spacer to facilitate manipulation thereof; and (f) said spacer being formed from a non-metallic material which is biologically inactive.

8. In a biologically inactive non-metal spinal fusion interbody spacer including an anterior end surface, a posterior end surface spaced from said anterior end surface, a superior abutment surface, and an inferior abutment surface spaced from said superior abutment surface, said superior and inferior abutment surfaces extending respectively between said anterior and posterior end surfaces; the improvement comprising:

(a) at least one of said abutment surfaces being effectively convex between said end surfaces;

(b) said one of said abutment surfaces which is effectively convex is formed by a plurality of substantially planar facets;

(c) a center reference plane positioned substantially equidistant between said anterior and posterior end surfaces and intersecting said superior and inferior abutment surfaces;

(d) said one of said abutment surfaces which is effectively convex having a respective peak of convexity located at a position spaced substantially anterior of said center reference plane; and (e) said spacer being formed of a non-metallic material which is biologically inactive.

9. In a biologically inactive non-metal spinal fusion interbody spacer including an anterior end surface, a posterior end surface spaced from said anterior end surface, a superior abutment surface, and an inferior abutment surface spaced from said superior abutment surface, said superior and inferior abutment surfaces extending respectively between said anterior and posterior end surfaces; the improvement comprising:

(a) at least one of said abutment surfaces being effectively convex between said end surfaces;

(b) a center reference plane positioned substantially equidistant between said anterior and posterior end surfaces and intersecting said superior and inferior abutment surfaces;

(c) said one of said abutment surfaces which is effectively convex having a respective peak of convexity located at a position spaced substantially anterior of said center reference plane;

(d) a pair of laterally opposite side surfaces;

(e) each of said opposite side surfaces being substantially concave; and (f) said spacer being formed of a non-metallic material which is biologically inactive.

10. In a biologically inactive non-metal spinal fusion interbody spacer including an anterior end surface, a posterior end surface spaced from said anterior end surface, a superior abutment surface, and an inferior abutment surface spaced from said superior abutment surface, said superior and inferior abutment surfaces extending respectively between said anterior and posterior end surfaces; the improvement comprising:
(a) at least one of said abutment surfaces being effectively convex between said end surfaces;
(b) a center reference plane positioned substantially equidistant between said anterior and posterior end surfaces and intersecting said superior and inferior abutment surfaces;
(c) said one of said abutment surfaces which is effectively convex having a respective peak of convexity located at a position spaced substantially anterior of said center reference plane;
(d) a pair of laterally opposite side surfaces;
(e) each of said opposite side surfaces being substantially concave and cylindrical; and
(f) said spacer being formed of a non-metallic material which is biologically inactive.

11. In a biologically inactive non-metal spinal fusion interbody spacer including an anterior end surface, a posterior end surface spaced from said anterior end surface, a superior abutment surface, and an inferior abutment surface spaced from said superior abutment surface, said superior and inferior abutment surfaces extending respectively between said anterior and posterior end surfaces; the improvement comprising:
(a) at least one of said abutment surfaces being effectively convex between said end surfaces;
(b) a center reference plane positioned substantially equidistant between said anterior and posterior end surfaces and intersecting said superior and inferior abutment surfaces;
(c) said one of said abutment surfaces which is effectively convex having a respective peak of convexity located at a position spaced substantially anterior of said center reference plane;
(d) said anterior end surface and said posterior end surface are of the same height; and
(e) said spacer being formed of a non-metallic material which is biologically inactive.

12. In a biologically inactive non-metal spinal fusion interbody spacer including an anterior end surface, a posterior end surface spaced from said anterior end surface, a superior abutment surface, and an inferior abutment surface spaced from said superior abutment surface, said superior and inferior abutment surfaces extending respectively between said anterior and posterior end surfaces; the improvement comprising:
(a) at least one of said abutment surfaces being effectively convex between said end surfaces;
(b) a center reference plane positioned substantially equidistant between said anterior and posterior end surfaces and intersecting said superior and inferior abutment surfaces;
(c) said one of said abutment surfaces which is effectively convex having a respective peak of convexity located at a position spaced substantially anterior of said center reference plane;
(d) a pair of laterally opposite side surfaces spaced apart by an effective width dimension;
(e) said superior and inferior abutment surfaces being spaced apart an effective height dimension;
(f) said height dimension being greater than said width dimension; and
(g) said spacer being formed of a non-metallic material which is biologically inactive.

13. A biologically inactive non-metal spinal fusion interbody spacer comprising:
(a) a body having superior and inferior surfaces;
(b) at least one of said surfaces being generally convex from front to rear of said spacer and having a greatest height located between the front and the rear of said device;
(c) said one surface is greatest in height between said front and a front to rear center of said device;
(d) said one surface is formed by a plurality of substantially planar facets; and
(e) said spacer being formed of a non-metallic material which is biologically inactive.

14. A biologically inactive non-metal spinal fusion interbody spacer comprising:
(a) an anterior end surface and an opposite posterior end surface spaced from said anterior end surface;
(b) a superior abutment surface and an opposite inferior abutment surface spaced from said superior abutment surface, said superior and inferior abutment surfaces extending respectively between said anterior and posterior end surfaces;
(c) at least one of said abutment surfaces being effectively convex between said end surfaces such that said spacer is greatest in height at a medial location between and spaced from both of said anterior and posterior surfaces;
(d) said spacer being formed of a non-metallic material which is biologically inactive;
(e) a center reference plane positioned substantially equidistant between said anterior and posterior end surfaces and intersecting said superior and inferior abutment surfaces; and
(f) said one of said abutment surfaces is effectively convex having a peak of convexity located at a position spaced substantially anterior of said center reference plane and posterior of said anterior end surface.

15. A biologically inactive non-metal spinal fusion interbody spacer comprising:
(a) an anterior end surface and an opposite posterior end surface spaced from said anterior end surface;
(b) a superior abutment surface and an opposite inferior abutment surface spaced from said superior abutment surface, said superior and inferior abutment surfaces extending respectively between said anterior and posterior end surfaces;
(c) at least one of said abutment surfaces being effectively convex between said end surfaces such that said spacer is greatest in height at a medial location between and spaced from both of said anterior and posterior surfaces;
(d) said spacer being formed of a non-metallic material which is biologically inactive;
(e) a center reference plane positioned substantially equidistant between said anterior and posterior end surfaces and intersecting said superior and inferior abutment surfaces; and
(f) each of said abutment surfaces being effectively convex and having a respective peak of convexity located at a position spaced substantially anterior of said center reference plane.

16. A biologically inactive non-metal spinal fusion interbody spacer comprising:
(a) an anterior end surface and an opposite posterior end surface spaced from said anterior end surface;
(b) a superior abutment surface and an opposite inferior abutment surface spaced from said superior abutment surface, said superior and inferior abutment surfaces extending respectively between said anterior and posterior end surfaces;
(c) at least one of said abutment surfaces being effectively convex between said end surfaces such that said spacer is greatest in height at a medial location between and spaced from both of said anterior and posterior surfaces;
(d) a pair of laterally opposite side surfaces;
(e) each of said opposite side surfaces being substantially concave; and
(f) said spacer being formed of a non-metallic material which is biologically inactive.

17. A biologically inactive non-metal spinal fusion interbody spacer comprising:
(a) an anterior end surface and an opposite posterior end surface spaced from said anterior end surface;
(b) a superior abutment surface and an opposite inferior abutment surface spaced from said superior abutment surface, said superior and inferior abutment surfaces extending respectively between said anterior and posterior end surfaces;
(c) at least one of said abutment surfaces being effectively convex between said end surfaces such that said spacer is greatest in height at a medial location between and spaced from both of said anterior and posterior surfaces;
(d) a pair of laterally opposite side surfaces;
(e) each of said opposite side surfaces being substantially concave and cylindrical; and
(f) said spacer being formed of a non-metallic material which is biologically inactive.

18. A biologically inactive non-metal spinal fusion interbody spacer comprising:
(a) an anterior end surface and an opposite posterior end surface spaced from said anterior end surface;
(b) a superior abutment surface and an opposite inferior abutment surface spaced from said superior abutment surface, said superior and inferior abutment surfaces extending respectively between said anterior and posterior end surfaces and being greatest in height at a medial location between and spaced from said anterior and posterior end surfaces;
(c) a center reference plane positioned substantially equidistant between said anterior and posterior end surfaces and intersecting said superior and inferior abutment surfaces;
(d) each of said abutment surfaces being effectively convex and having a respective peak of convexity located at said medial location spaced substantially anterior of said center reference plane; and
(e) said spacer being formed from a non-metallic material which is biologically inactive.

19. In a biologically inactive non-metal spinal fusion interbody spacer including an anterior end surface, a posterior end surface spaced from said anterior end surface, a superior abutment surface, and an inferior abutment surface spaced from said superior abutment surface, said superior and inferior abutment surfaces extending respectively between said anterior and posterior end surfaces; the improvement comprising:
(a) at least one of said abutment surfaces being effectively convex between said end surfaces;
(b) a center reference plane positioned substantially equidistant between said anterior and posterior end surfaces and intersecting said superior and inferior abutment surfaces;
(c) said one of said abutment surfaces which is effectively convex having a respective peak of convexity wherein said spacer is of greatest height located at a position spaced substantially anterior of said center reference plane and spaced from said anterior end; and
(d) said spacer being formed of a non-metallic material which is biologically inactive.

20. A spacer as set forth in claim 14 wherein:
(a) said one of said abutment surfaces which is effectively convex is non-threaded and formed by a plurality of substantially planar facets.

21. A spacer as set forth in claim 14 and including:
(a) at least one opening for receiving a bone fusion material to promote fusion between a pair of adjacent vertebrae.

22. A spacer as set forth in claim 14 and including:
(a) a pair of laterally opposite side surfaces spaced apart by an effective width dimension;
(b) said superior and inferior abutment surfaces being spaced apart an effective height dimension; and
(c) said height dimension being greater than said width dimension.

23. A spacer as set forth in claim 19 and including:
(a) each of said abutment surfaces being effectively convex and having a respective peak of convexity located at a position spaced substantially anterior of said center reference plane.

24. The spacer according to claim 9 wherein:
(a) said one surface is shaped to generally mate with a concave vertebral surface during use.

25. The spacer according to claim 9 wherein:
(a) both of said surfaces are convex from front to rear of said device.

26. The spacer according to claim 9 wherein:
(a) said spacer is constructed of a single, unitary and solid structure.

* * * * *